(12) United States Patent
Miller et al.

(10) Patent No.: US 9,259,154 B2
(45) Date of Patent: Feb. 16, 2016

(54) MONITORING METHOD AND APPARATUS (75) Inventors: Robin Miller, Abingdon (GB); Alison Burdett, Abingdon (GB)

(73) Assignee: Toumaz Technology Limited, Abingdon, Oxfordshire (GB)

( * ) Notice: Subject to any disclaimer, the term of this patent is extended or adjusted under 35 U.S.C. 154(b) by 1688 days.

(21) Appl. No.: 12/088,200

(22) PCT Filed: Sep. 6, 2006

(86) PCT No.: PCT/GB2006/050278
§ 371 (c)(1),
(2), (4) Date: Mar. 26, 2008

(87) PCT Pub. No.: WO2007/036748
PCT Pub. Date: Apr. 5, 2007

(65) Prior Publication Data
US 2008/0214946 A1    Sep. 4, 2008

(30) Foreign Application Priority Data

Sep. 27, 2005    (GB) .................................. 0519649.8

(51) Int. Cl.
*A61B 5/0468*  (2006.01)
*A61B 5/00*  (2006.01)
*A61B 5/0452*  (2006.01)
A61B 5/0245  (2006.01)
A61B 5/0476  (2006.01)

(52) U.S. Cl.
CPC ........... *A61B 5/0006* (2013.01); *A61B 5/04525* (2013.01); *A61B 5/0245* (2013.01); *A61B 5/0476* (2013.01); *A61B 5/7239* (2013.01); *A61B 5/7242* (2013.01); *A61B 5/7264* (2013.01); *A61B 2560/0209* (2013.01)

(58) Field of Classification Search
USPC ......................................................... 600/509
See application file for complete search history.

(56) References Cited

U.S. PATENT DOCUMENTS

| 5,092,340 | A | 3/1992 | Yamaguchi et al. |
| 5,273,049 | A | 12/1993 | Steinhaus et al. |
| 6,480,743 | B1 * | 11/2002 | Kirkpatrick et al. ............ 607/45 |

(Continued)

FOREIGN PATENT DOCUMENTS

| EP | 0545628 | 6/1993 |
| EP | 0941695 | 9/1999 |

(Continued)

OTHER PUBLICATIONS

PCT International Search Report for International Application No. PCT/GB2006/050278, 4 pages.

(Continued)

*Primary Examiner* — Alyssa M Alter (57) ABSTRACT

Apparatus for monitoring an ECG signal comprises a first body wearable part 1 for receiving a physiological signal and comprising processing means, a memory, and a wireless transceiver, the memory storing a plurality of signal segment templates. The processing means is arranged to compare and match segments of the physiological signal to the stored template. The apparatus further comprises a second part 4 comprising a wireless transceiver and processing means, the processing means being arranged to generate and/or modify signal segment templates, and to cause said transceiver of the second part to transmit generated or modified templates to the first part.

14 Claims, 9 Drawing Sheets

(56) References Cited

U.S. PATENT DOCUMENTS

| | | |
|---|---|---|
| 6,858,006 B2 | 2/2005 | MacCarter et al. |
| 2002/0013614 A1* | 1/2002 | Thompson ............ 607/60 |
| 2004/0243014 A1* | 12/2004 | Lee et al. ............ 600/510 |
| 2005/0192506 A1* | 9/2005 | Kim et al. ............ 600/510 |
| 2006/0074331 A1* | 4/2006 | Kim et al. ............ 600/515 |

FOREIGN PATENT DOCUMENTS

| | | |
|---|---|---|
| JP | 2003-220045 | 8/2003 |
| JP | 2004-152002 | 5/2004 |
| WO | WO-93/19667 A1 | 10/1993 |
| WO | WO-2005/030268 | 4/2005 |
| WO | WO-2006/039694 | 4/2006 |

OTHER PUBLICATIONS

EP Search Report for Application No. GB0519649.8, 1 page.
PCT International Report on Patentability for International Application No. PCT/GB2006050278, 10 pages.
Chun, Yi Lee et al., "Ultra-low power UWB for real time biomedical wireless sensing", Circuits and Systems, 2005. ISCAS 2005. IEEE International Symposium on Kobe, USA, IEEE, May 23, 2005, Piscataway, NJ, pp. 57-60.
Hamilton, P., "Open Source ECG Analysis", Computers in Cardiology 2002, vol. 29 (Cat. No. 02CH37421) IEEE Piscataway, NJ, USA, 2002, pp. 101-104.
JP Office Action for 2008-532881, Oct. 2, 2012, 4 unnumbered pages.

* cited by examiner

MONITORING METHOD AND APPARATUS

FIELD OF THE INVENTION

The present invention relates to a monitoring method and apparatus and in particular, though not necessarily, to a method and apparatus for monitoring physiological signals whether electrical or biochemical.

BACKGROUND TO THE INVENTION

The Electro-Cardiogram or ECG has long provided a means for monitoring and diagnosing patient conditions. Traditionally, ECGs have been recorded by attaching two or more electrodes to a patient's chest, performing some signal processing on the recorded signal such as filtering to remove noise, and recording the processed result. Considering the case of a patient with a suspected heart condition, one way to diagnose the condition is to continuously record ECG data for some period of time, e.g. several hours, and for a physician to study the recorded data to identify any anomalies. This is inconvenient for the patient as the data collection systems tend to be large and therefore the patient must remain in the same location for the duration of the process, and is time consuming on the part of the physician.

To overcome these problems, relatively sophisticated signal processing techniques have been developed to analyse substantially real time ECG data to classify heart beats as either normal or abnormal, and to record only the occurrence and type of an abnormal heart beat. As the data storage requirements are massively reduced—only event and type data rather than continuous signals need to be recorded—the recording apparatus can be made portable and even wearable, whilst physicians are presented with a simple classification of heart beat events which makes diagnosis easier and quicker.

It is known, for example, to provide a wearable computer device which may be around the size of a pack of cards, and which is coupled to a pair of chest worn electrodes. The computer device compares recorded heartbeats against a number of stored "template heartbeats" and uses the results to classify the recorded heartbeats. An ongoing count is maintained of the heartbeats matching each template. Heartbeats that do not match any template may be stored for future analysis. However, as these unmatched templates can be expected to occur only infrequently, the data storage requirements are not excessive. The heartbeat classification process is computationally intensive and therefore consumes a relatively large amount of power. However, this power requirement can generally be provided by a battery located within the computer device.

Whilst representing a considerable advance over systems of the type that require a patient to remain at a particular location, portable monitoring systems of this type are still relatively bulky. One approach to making the monitoring systems more user friendly might be to configure them as two part systems, with a first relatively small and wearable part being coupled to the monitoring electrodes and transmitting the monitored ECG signal over a wireless link to a second, larger data processing device (which may be carried in a pocket or may be left elsewhere within the same locality, i.e. within range of the worn part). However, the power required to allow continuous broadcast of ECG signals will place a limit both on the size of the wearable part and on the battery lifetime. Furthermore, if the wearer moves out of range of the data processing device, data will be lost.

It will be appreciated that analogous problems will arise with systems for monitoring other physiological "conditions" such as electro-encephelogrammes (EEGs), blood glucose levels, etc (where bioelectrical transducers such as biosensors are used to convert a biochemical parameter into an electrical signal). A solution to these problems may also find applications in non-medical areas such as industrial process control.

SUMMARY OF THE INVENTION

It is an object of the present invention to overcome or at least mitigate the disadvantages of known two-part monitoring systems. It is an object of the invention to provide a two-part monitoring system having a component that is extremely small and which can be worn on a user's body for a prolonged period.

According to a first aspect of the present invention there is provided an apparatus for monitoring a condition, the apparatus comprising:

a first part comprising
a wireless transceiver,
a memory for storing a plurality of signal segment templates,
an input for receiving an electrical signal, and
processing means for segmenting a received electrical signal into signal segments, for determining whether or not each segment matches one of said stored templates, and for causing said transceiver to transmit the results of the matching operation over a wireless link;
a second part comprising
a wireless transceiver for receiving data transmitted from said first part over said wireless link,
a memory for storing the received data or other data generated using the received data,
processing means for generating or modifying signal segment templates and for causing said transceiver to transmit to the first part the generated or modified templates.

Preferably, the results of the matching operation sent to the second part comprise identities of matched templates. Data may be collected and stored at the first part, and periodically transmitted to the second part. Data may be sent in the form of template identities and numbers of occurrences of these identities. An updated template may also be sent from the first part to the second part at defined intervals.

Preferably, said processing means is arranged to cause a signal segment to be transmitted to the second part in the event that a template is not matched to that signal segment. The segment may be stored in the memory of the first part prior to transmission, or sent immediately.

The processing means may be arranged to analyse a signal segment for abnormalities and to cause the signal segment to be transmitted to the second part if an abnormality is detected, even when a template match has been found. Again, the segment may be stored for later transmission, or sent immediately.

Said processing means of the first part may be arranged to record in said memory a sequence of recent signal segments for use in subsequent analyses.

Preferably, said processing means of the first part is arranged to detect when the first part is out of communication range and in such an event to store data which would otherwise have been transmitted to the second part. The processing means detects when the second part is back in range, and thereafter sends the stored data.

Preferably, said processing means of the second part is arranged to receive signal segments transmitted from the first part, and to use these segments to generate or modify signal segment templates for transmission to the first part. More preferably, templates are stored in said memory of the second part.

Preferably, said processing means of the second part is arranged to synchronise the templates stored in the memory of the second part with those stored in the memory of the first part. In the event that the memory of the first part has no templates stored therein, all templates stored in the memory of the second part will be transmitted to the first part.

Preferably, said apparatus is suitable for monitoring a mammalian ECG. Said first part may comprise two or more electrodes coupled to said input for providing an ECG signal. Said processing means is arranged to segment the signal into individual heartbeats. The segments may or may not be contiguous.

The processing means of the first part may be arranged to determine the RR interval of the ECG signal. The RR interval may be used to detect abnormalities in ECG segments, and/or may be transmitted to the second part.

According to a second aspect of the present invention there is provided apparatus for monitoring a physiological condition, the apparatus comprising:
  a first body wearable part for receiving a physiological signal and comprising processing means, a memory, and a wireless transceiver, the memory storing a plurality of signal segment templates, and the processing means being arranged to compare and match segments of the physiological signal to the stored templates; and
  a second part comprising a wireless transceiver and processing means, the processing means being arranged to generate and/or modify signal segment templates, and to cause said transceiver of the second part to transmit generated or modified templates to the first part.

According to a third aspect of the present invention there is provided a method of monitoring a condition, the method comprising:
  at a first part
  receiving a signal indicative of said condition;
  segmenting the signal into successive signal segments;
  comparing each signal segment against one or more of a set of signal segment templates and identifying any matching templates;
  sending identities of matching templates via a wireless communication link to a second part;
  at the second part
  storing received data;
  generating new or modified signal segment templates and transmitting these via said wireless communication link to the first part,
  and at the first part
  storing received new or modified templates for subsequent use.

Preferably, the method comprises transmitting a signal segment from the first part to the second part in the event that a template match is not found for the signal segment or if a match is found but an abnormality is detected in the signal segment.

Preferably, the first part collects matching template identities and numbers of occurrences and periodically transmits these to the second part. Signal segments requiring transmission to the second part may also be collected and sent periodically. Data may be stored at the first part when the second part is out of range or otherwise unable to communicate with the first part, and sent to the second part when communication can resume.

DETAILED DESCRIPTION OF CERTAIN EMBODIMENTS OF THE INVENTION

Figure 1:
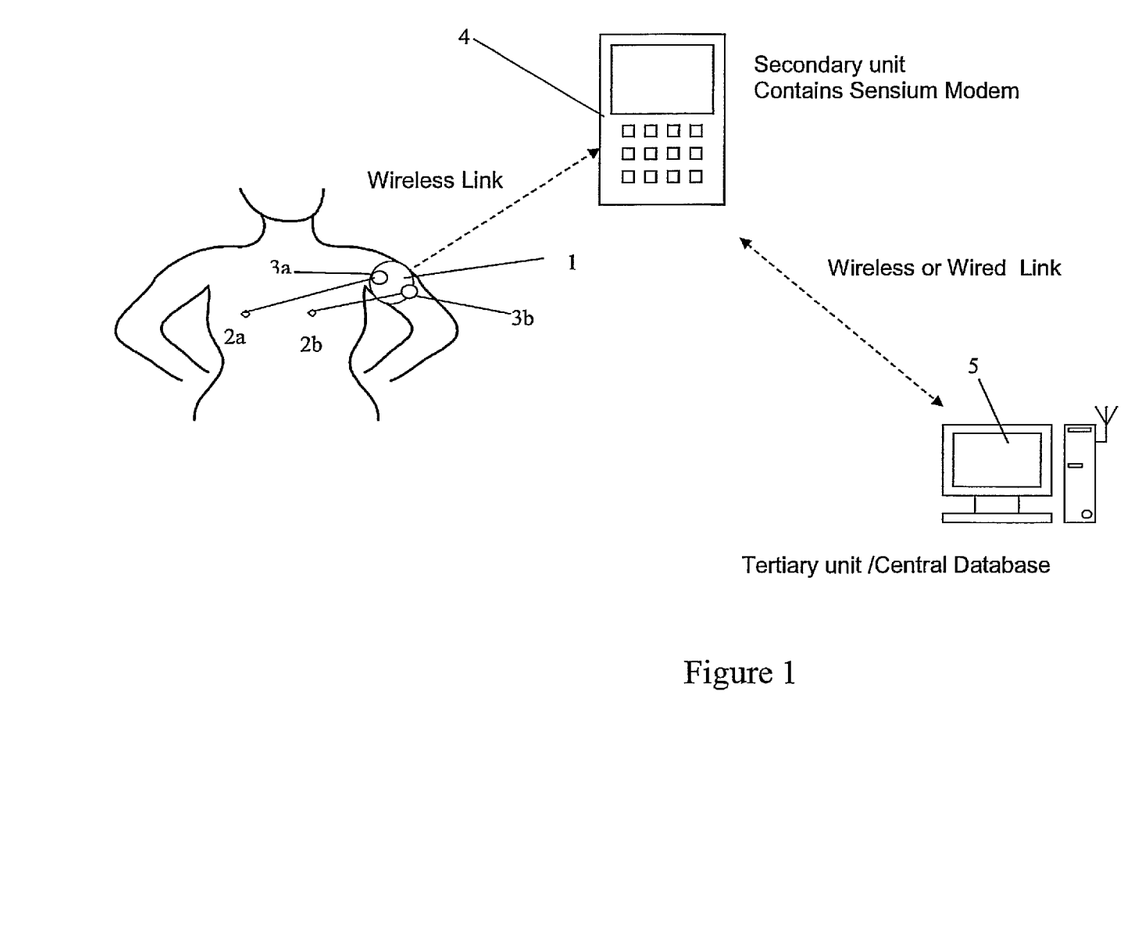
FIG. 1 illustrates schematically a public healthcare system.

There is illustrated in FIG. 1 a two-part ECG monitoring system which is one component of a public healthcare system. A first part 1, referred to here as the "digital plaster", resembles a conventional plaster for covering a wound or other minor injury. The digital plaster 1 is provided on one side with an adhesive that allows a user to stick the plaster to his or her skin. As will be described in more detail below, the plaster comprises inputs 2a,2b for coupling to respective electrodes 3a,3b to receive ECG signals, signal processing means, and a transceiver for communicating over a wireless link with a second part, or "base station", 4. The electrodes are preferably integrated into the plaster 1, but may be separate from the plaster and coupled to it by suitable leads. The digital plaster is powered by a suitable battery, e.g. a 1V zinc air battery. Advances in technology may, in the future, allow the plaster to be self-powered, e.g. using some bio-electrical cell or using the body's electromagnetic fields.

The base station 4 may be a custom designed and built module, or may be a generic piece of hardware with dedicated software running on it, e.g. a PDA or smart phone. In either case, the role of the base station 4 is to communicate with the plaster 1 over the wireless link for the purpose of recording and processing ECG data sent from the plaster 1, and configuring the operation of the digital plaster 1. The base station 4 should be suitable for carrying in a pocket or handbag or for wearing on a belt, although the design of the system is such that it can be left for prolonged periods outside of the range of the wireless link without significantly impacting on the required operation of the system.

FIG. 1 also illustrates a third system component 3 in the form of a central database 5. The base station 4 may periodically communicate with the central database 5, e.g. over a cellular telephone network, to transfer recorded ECG data to the database. This operation will allow physicians or other medical staff to remotely review the recorded data. Such a central database may manage many thousands of individual monitoring systems. Procedures for communicating between the central database and the individual monitoring systems will be readily apparent, as will the procedures for collecting and analysing data at the central database, and as such will not be described further here.

Figure 2:
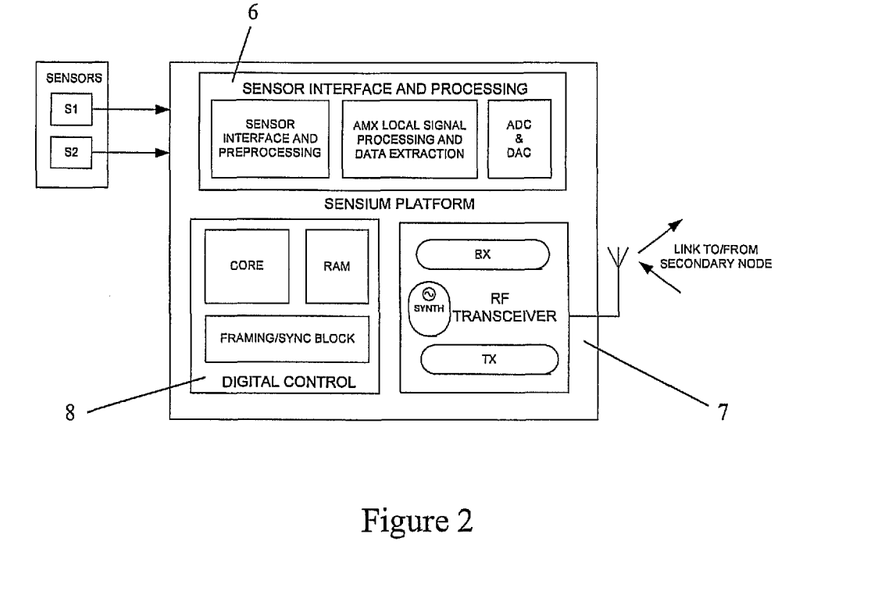
FIG. 2 illustrates schematically a first part or digital plaster of the system of FIG. 1.
Figure 3:
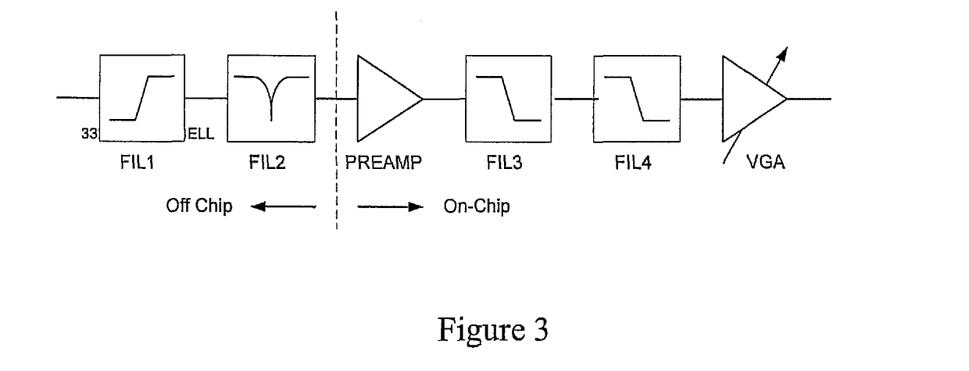
FIG. 3 illustrates a sensor interface and preprocessing circuit of the digital plaster of FIG. 2.

FIG. 2 illustrates in functional terms the "architecture" of the digital plaster 1. Three major processing blocks can be identified:
  Sensor Interface and Processing 6
  The sensor signal received from the electrodes 3a,3b is preconditioned (i.e. amplified, filtered etc.) such that it is in a suitable form for the signal processing block. This is performed using the analogue circuit illustrated schematically in FIG. 3, where:

FIL1: A passive high pass filter, corner frequency around 0.5 Hz.

FIL2: A notch filter to eliminate mains noise (50/60 Hz) which may be at a much higher level than the actual ECG signal.

PREAMP: Low level ECG signals are amplified by a suitable gain (typically) of 50 to 100.

FIL3: This passive lowpass filter is effectively an anti-alias filter for the subsequent switched capacitor filter stage FIL4. In practice the pole of FIL3 will be incorporated into the PREAMP and is effectively the bandwidth (500 Hz) of this preamplifier.

FIL4: A lowpass filter to limit the ECG signal to frequencies of interest and eliminate high frequency noise. The cut-off frequency is programmable, e.g. to one of 100-200-300 Hz. This will be a switched capacitor design to minimise chip area and maximise signal handling at low supply voltages.

VGA: A final stage of variable gain may be required to ensure that signal levels input to the subsequent data processing stage are substantially constant.

The local signal processing and data extraction block performs local signal processing, analysing the ECG waveform to detect whether the current heart beat is classified as normal or arrhythmic according to a pre-defined set of detection rules described in detail below.

RF Transceiver 7

This functional block enables communication between the digital plaster 1 and the base station 4. Any appropriate transmission protocol(s) can be used to transmit data including Bluetooth™, UWB, and proprietary protocols. Sensor status information, ECG summary data (i.e. template matching results) or the complete ECG waveform can be transmitted from the digital plaster 1 to the base station 4, whilst configuration and control parameters can be transmitted back from the base station 4 to the digital plaster 1. These control parameters can alter the users arrhythmia detection settings, change the digital plaster's operation from local processing to transparent mode, request status information (e.g. battery lifetime), etc.

Controller 8

A digital controller 8 performs various control, configuration and timing functions and updates the plaster operation when commands are received from the base station 4. The control block 8 also contains local memory (RAM) for storing short segments of the ECG waveform (e.g. 15 seconds preceding the current processed beat), plus user-specific parameters for analysis and classification of the ECG waveform.

Figure 4:
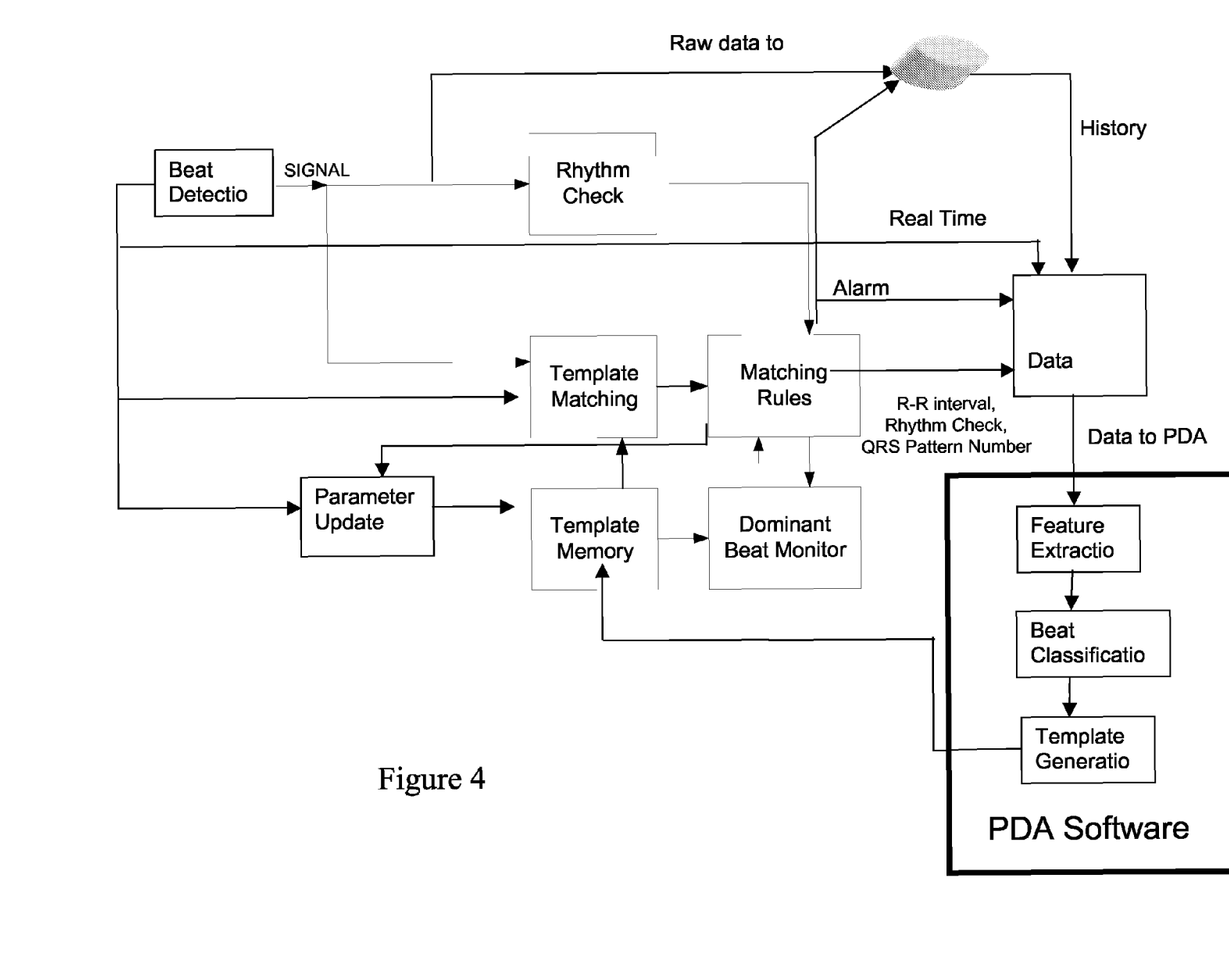
FIG. 4 is a functional block diagram of the digital plaster of FIG. 2.

Considering further the local signal processing and data extraction functionality of the sensor interface and processing block 6, this relies substantially on the Open Source ECG Analysis (OSEA) model, P. S. Hamilton, 'Open Source ECG Analysis Software (OSEA) Documentation', www.eplimited.com. FIG. 4 illustrates this model in very general terms, where the main steps are as follows:

Beat Detection

Figure 5:
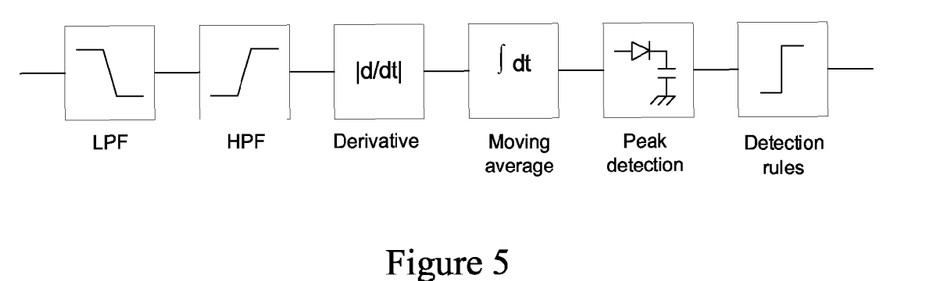
FIG. 5 illustrates functional components of a QRS detection process of the digital plaster of FIG. 2.

A received ECG signal is first analysed to determine when a heartbeat is present. More particularly, it determines when a QRS complex of a heartbeat is present. FIG. 5 shows the basic functions required to implement QRS detection within the OSEA model. Following filtering, the absolute value of the signal is averaged over a given time window. The averaging window is chosen to be roughly the width of a typical QRS complex. Setting the window to less than 150 ms produces the best results. The LPF cut-off is around 16 Hz, while the HPF cut-off is around 8 Hz. The LPF, HPF and derivative combine to produce a bandpass filter with a passband from 5 to 11 Hz, roughly the bandwidth that contains most of the energy in the QRS complex.

After the performing the moving average, the signal effectively produces a 'lump' every time a QRS complex occurs. T-waves may also produce lumps but these are generally smaller than those due to QRS complexes. A peak detector locates the position of the 'lumps', and after detection the peak is classified as either a QRS complex or noise, or it is saved for later classification. The detection algorithm uses the peak height, peak location and maximum derivative to classify the peaks, following the algorithm shown in FIG. 6.

Figure 6:
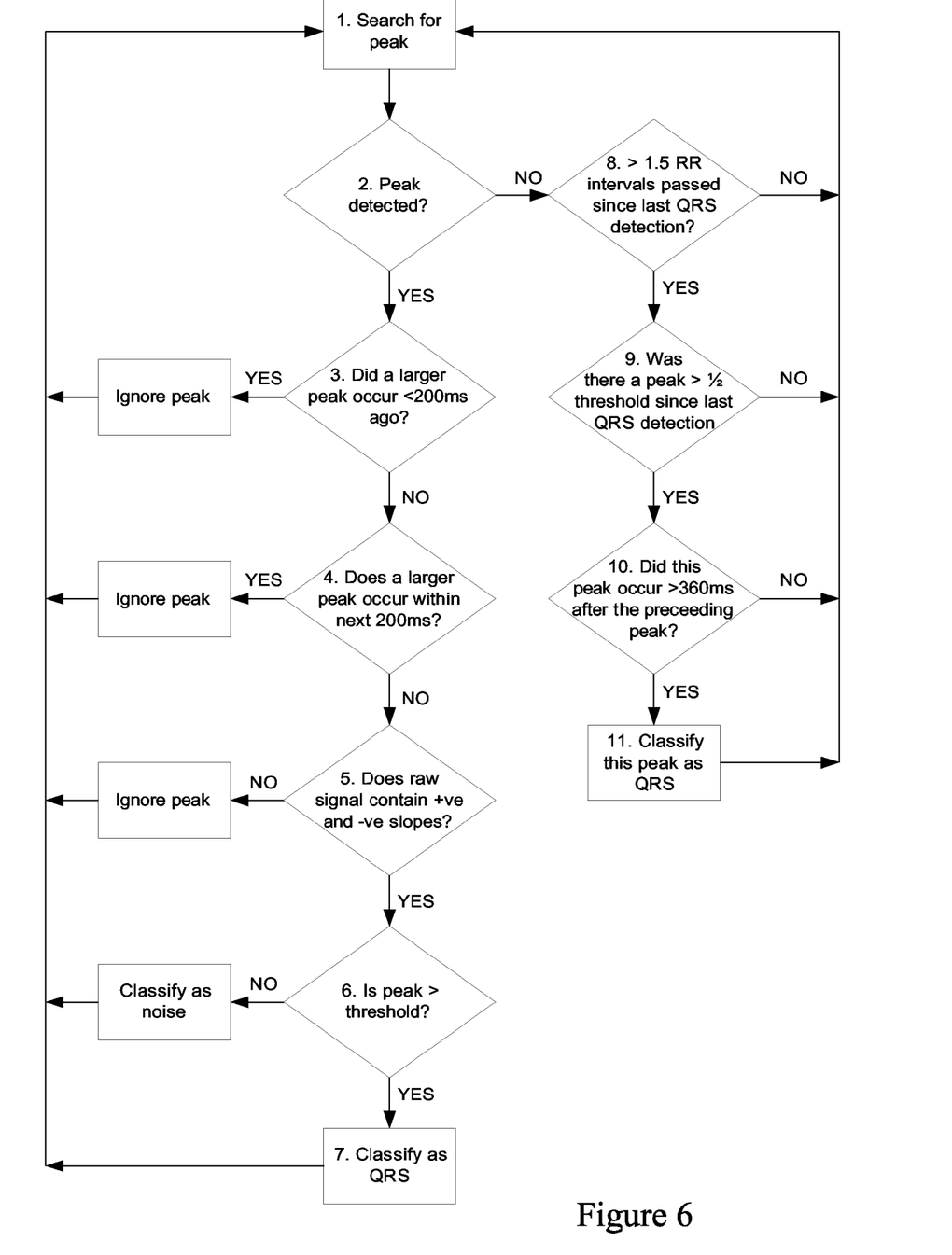
FIG. 6 is a flow diagram illustrating a QRS detection algorithm of the process of FIG. 5.

The algorithm of FIG. 6 requires that a detection threshold is calculated to allow peaks to be classified either as QRS complexes or as noise. Every time a peak is classified as QRS it is added to a buffer containing the 8 most recent QRS peaks, and the RR interval is added to a buffer containing the 8 most recent RR intervals. Every time a peak is classified as noise it is added to a buffer containing the 8 most recent noise peaks. The detection threshold (DET_TH) is set between the mean or median of the noise peak and QRS peak buffer values according to the formula:

$$DET\_TH = nAVG + TH*(qAVG - nAVG)$$

where nAVG and qAVG are the averages of the most recent 8 noise and QRS peak values respectively, and TH is a threshold coefficient. The average of each of these values can be calculated either as a mean or median value. Calculating the mean of the QRS peaks, noise peaks and RR intervals results in simpler calculations and actually improves QRS detector performance. However, calculating the median of the QRS and noise peaks has been shown to give improved performance when the QRS detector is combined with the beat classification algorithm. It may therefore be advisable to allow the averaging function (i.e. either mean or median) to be selected.

On start-up, the first eight peaks detected are classified as QRS peaks, and the noise peak buffer is set to zero. The eight most recent RR intervals are set to one second. In addition, if no peaks are detected for eight seconds the detection thresholds are re-initialised in the manner described above. This is because it is possible (if very rare) that a string of large ventricular beats may raise the detection thresholds so much that normal low amplitude beats that follow are ignored.

Once a beat (i.e. a QRS complex) is detected, the algorithm will also indicate how many new samples have occurred since the QRS complex was detected, i.e. it will indicate the time location of the R wave. This is necessary because the beat detection algorithm depicted in FIG. 6 has a variable detection delay. Referring to FIG. 6, if a QRS peak is detected at step 7, the detection delay will be roughly the sum of the filter delays, the moving window integration width, and the 200 ms delay required for checking at step 4. This gives a total detection delay of typically 395 ms. However if a QRS complex is detected at step 11 (also called a search back detection), the total delay will be this delay plus half the average RR interval, which could be as much as one second. For wearable monitoring applications which simply report heart rate, this variable detection delay is not perceived as a major issue. However for some applications a relatively long, variable delay can be a problem. For example in patient monitoring, the visible heart beat indication should coincide more closely with the pulse felt at the wrist (typically within 250 ms detection delay).

One option is to disable the search back part of the algorithm, and to simply not report decisions that are detected from search back. This will give a fixed detection delay of around 395 ms. If search back detections are ignored (and the detection threshold TH is appropriately adjusted), the QRS detection sensitivities are still close to 99.7%. The majority of the remaining delay occurs because after each peak detection, the algorithm waits 200 ms to see if a larger peak occurs within the QRS refractory period. A simpler option is to set a 200 ms blanking period after detection of a peak, which will result in a fixed detection delay of 195 ms. However this option will result in a reduced sensitivity since it allows large P waves to be detected as QRS complexes, and the following QRS complexes are then ignored because they occur during the 200 ms blanking period.

For the envisaged application, a variable detection delay is not seen as a major issue and thus it is proposed that the full algorithm be used. If a short detection delay is required, this full algorithm can be used to set thresholds for a simple, shot delay detection scheme. Selection of the full algorithm or short delay version could be programmable.

The Beat Detection block will indicate the time points of the R waves (the R wave location is also known as the "fiducial point").

Rhythm Check

This block receives the time points of the R waves from the Beat Detection block. The RR interval of the current beat is compared with previous RR beat intervals to determine the current rhythm. The rhythm check returns a classification of NORMAL, PVC (premature) or UNKNOWN. The result is passed to the matching rules block (see below).

Template Memory

A number of beat templates are stored in the template memory. These are passed to the plaster 1 by the base station 4.

Template Matching

The template matching block receives the time points of the R waves from the Beat Detection block, as well as the preconditioned ECG signal. The shape of the current beat is compared (e.g. using a correlation process) to one or more of the templates stored in the template memory to determine which (if any) of the stored templates the current beat most closely resembles. If the beat shape is close enough to one of the stored templates, the template ID is noted and the current beat is 'averaged' into the stored template.

Dominant Beat Monitor

The template number, rhythm and features of the last 180 beats are monitored to determine the dominant beat type. The dominant beat type is used to determine the order in which templates are selected from the template memory during template matching in order to expedite the matching process and hence reduce power consumption.

Matching Rules

Figure 7:
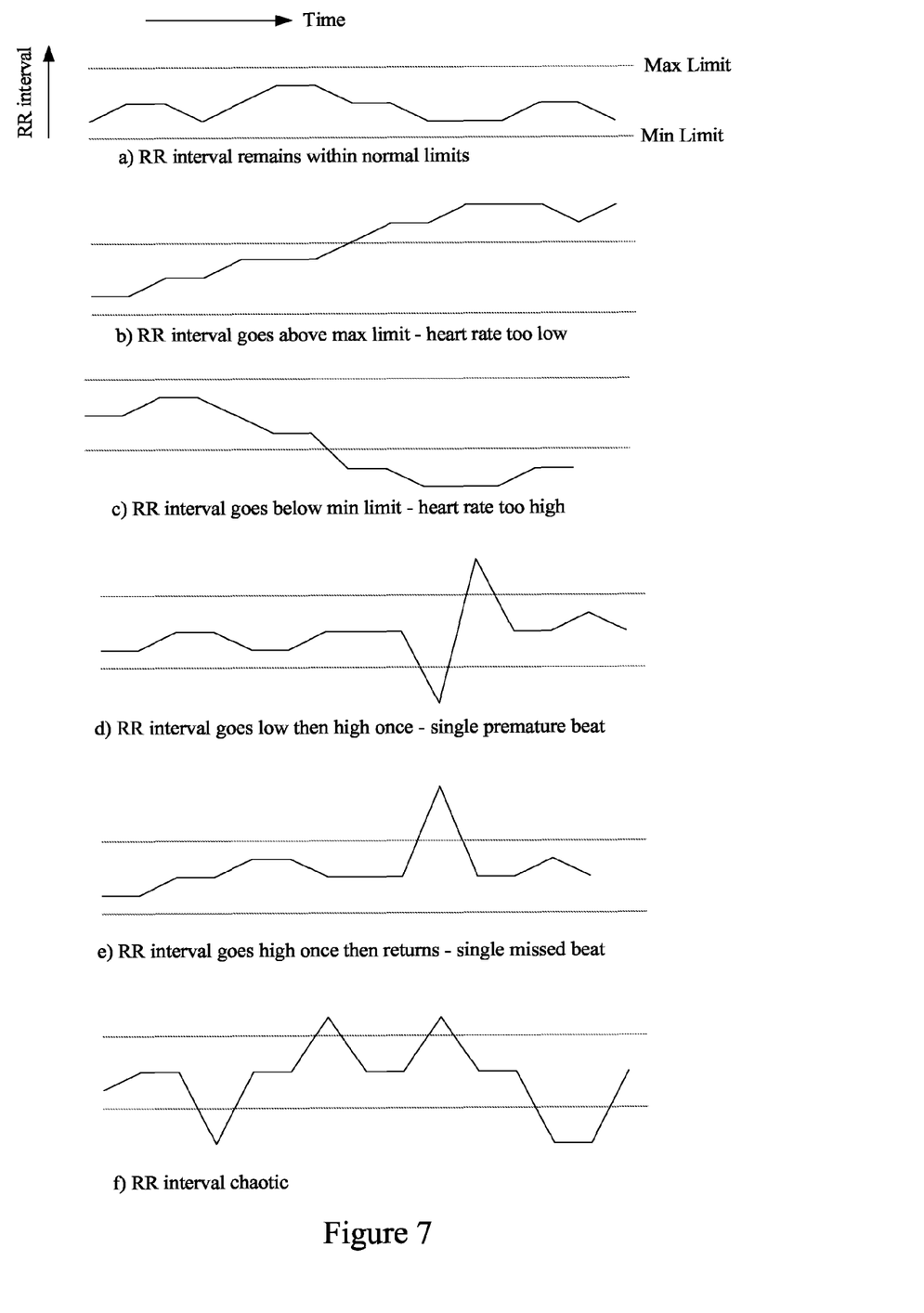
FIG. 7 illustrates a number RR trends indicative of respective heart conditions.

The matching rules define a set of rules for determining when a template matching operation must be performed. The matching rules are applied to the RR interval output of the Rhythm Check block to detect when (see FIG. 7):

a) average heart rate remains within normal limits;
b) average heart rate is low, below a given threshold (bradycardia);
c) average heart rate is high, above a given threshold (tachycardia);
d) beats occur prematurely (extrasystole or PVC);
e) beats are missed; and
f) heart rate is chaotic (fibrillation).

If conditions a) to e) are observed, the QRS waveform (or a section of signal referenced in time to the fiducial point) is matched against each template in the template memory to give some preliminary information regarding the medical condition of the heart. In the case of condition a), no alarm is triggered as the heartbeat is assumed to be normal. In the cases of conditions b) to e), as well as triggering a template matching operation, an alarm condition may be triggered. In the case of condition f), an alarm condition is triggered without requiring a template matching operation. Alarm conditions are sent to the base station.

In the case of conditions a) to e), in the event that a template match is found, the template ID is stored in memory for subsequent transmission to the base station. The RR interval may also be stored for later transmission. Typically, data may be collected in the memory of the plaster for some predefined time period, e.g. 30 seconds, before the saved data block is sent to the base station.

If, on the other hand, a template match is not found for a current beat, or in the case of condition f), the preconditioned ECG data which produced this result is immediately transmitted to the base station or stored in a "raw" data memory for subsequent transmission. The number of beats that can be stored in the plaster's memory will be limited by the size of the memory. It may be desirable to store some recent segment of historical data in the memory of the plaster, e.g. the last 30 beats. This may be useful when analysing an anomaly detected in a current beat, and may also be uploaded to the base station on request.

The above discussion has considered generally the implementation of the OSEA model in the digital plaster. Detailed consideration will now be given to an ultra-low power implementation of the digital plaster. Firstly, the QRS detection stage is considered, followed by a consideration of the beat classification stage.

Figure 8:
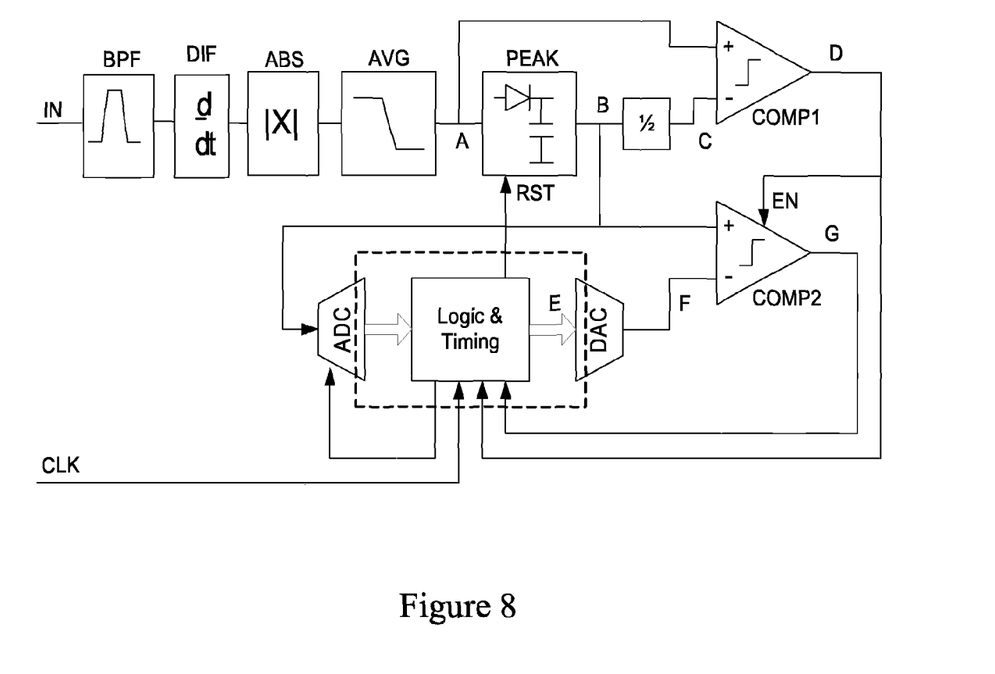
FIG. 8 illustrates schematically an ultra-low power mixed signal circuit architecture implementing a QRS detection stage.

The main steps required for QRS detection—band-pass filtering, peak detection and thresholding—could be implemented directly in mixed signal hardware. FIG. 8 indicates a mixed signal circuit architecture which will implement the required functionality. Peak detection and thresholding are performed in the analogue domain, while digital logic is used for timing and to implement basic decision rules. This circuitry effectively implements exactly the same algorithms as described in FIG. 5, but is now implemented using low power mixed signal hardware rather than by software.

Referring to FIG. 8, the sections of circuitry within the dashed line are digital, while all other blocks are analogue. The input ECG signal is bandpass filtered, the absolute value (magnitude) taken, and then passed through a lowpass filter which effectively performs an average. This filtered signal is fed to a peak detector; the output of the peak detector is divided by two (or any other suitable scaling factor, which may be selectable), and this 'half peak' at point C is compared against the filtered signal at point A. Thus the output of COMP1 (point D) will go high when the signal at A falls below that at point C, i.e. when the magnitude of the filtered signal drops to less than half the current peak value. The signal at D going high indicates that a peak has been found, and this signal acts as an enable for COMP2. COMP2 examines whether this peak value is above or below the current threshold value (point F); if the peak is higher than the threshold, the output of COMP2 (point G in FIG. 8) will go high.

When D goes high, indicating that a peak has been detected, the Logic & Timing block performs the following sequence of events:

The Logic & Timing block instructs the ADC to convert and latch the current peak value. This is stored as PEAK

[N]. The corresponding value of G is also stored as G[N]. The time between this peak and the last peak is stored as RR[N].

The Logic & Timing Block checks to see whether the previous peak value (PEAK[N−1]) occurred less than 200 ms ago, i.e. is RR[N]<200 ms. If the previous peak was within the last 200 ms, the previous peak amplitude must be greater than this peak (or the previous peak would have been discarded during the [N−1]$^{th}$ cycle), so this peak is discarded. The peak detector is reset, and the search continued for a new peak.

If the previous peak did not occur within the last 200 ms, i.e. RR[N]>200 ms, the Logic & Timing Block now resets the peak detector and peak interval counter, and waits to see whether the next ([N+1]$^{th}$) peak occurs within the following 200 ms.

If a new peak occurs within the next 200 ms, the ADC is instructed to convert and latch this peak value as PEAK [N+1]. The corresponding values of G[N+1] and RR[N+1] are also stored.

The Logic Block checks to see if PEAK[N+1]>PEAK[N]. If this is the case, then PEAK[N] (and G[N]) are discarded, and their values are replaced by PEAK[N+1] and G[N+1]. RR[N] is now set to RR[N]+RR[N+1]. However if PEAK[N+1]<PEAK[N], then PEAK[N+1], G[N+1] and RR[N+1] are discarded.

When the current value of PEAK[N] is determined, the Logic & Timing block checks to see if the corresponding value of G[N] is high or low. If high, then PEAK[N] is classified as a QRS pulse, and the value of PEAK[N] is added to the QRS buffer. If G[N] is low, then PEAK[N] is classified as noise, and PEAK[N] is added to the noise buffer.

The Logic & Timing block updates the threshold word E which is fed to the DAC to supply the analogue threshold voltage F to COMP2. Then the peak interval counter and peak detector are reset, and the search for a new ([N+1]$^{th}$) peak begins.

Figure 9:
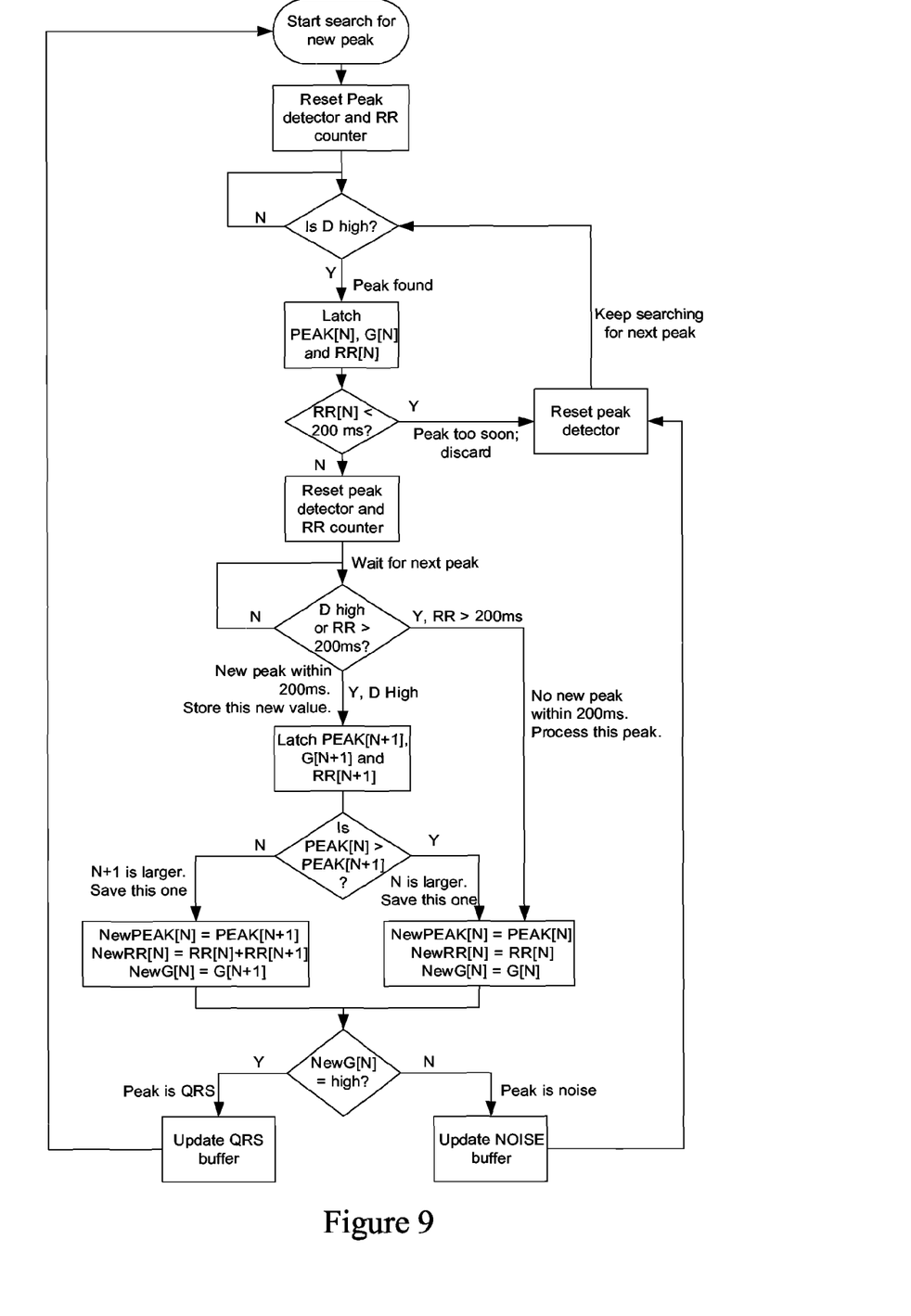
FIG. 9 is a flow diagram showing an algorithm for implementing logic and timing of the architecture of FIG. 8.

This decision process is illustrated in FIG. 9.

Re-examining the OSEA software, the most important parts of the beat classification algorithm (as illustrated in FIG. 4) are the rhythm check and template matching routines. In practice, if the current beat matches closely to a template shape that has been previously classified, then the current beat simply takes on the classification of the template. Feature extraction and the more complex classification rules are used to help classify beats which do not match to a template, or for beat shapes whose templates have not yet been classified.

The system described here shifts the burden of detecting and classifying new beat shapes to the base station. Thus the digital plaster needs simply to perform a rhythm check (simple digital logic) and also a template match. If the beat doesn't match any template, or the RR interval results in an alarm condition which overrides the need for template matching, the complete ECG waveform will be passed to the secondary unit for further feature extraction and classification. Once a new beat template shape is learnt and classified by the secondary unit, it will be passed back to the digital plaster.

The memory provided on the digital plaster is sufficiently large to allow it to record data (template IDs, RR intervals, and occasional ECG segments) for prolonged periods without communicating with the base station. This might be necessary when the digital plaster detects that the bases station is out of range. When the base station subsequently comes back within range, the stored data is uploaded to the bases station and the digital plaster's memories cleared. Whilst new templates cannot be generated and sent to the digital plaster during such times, the overall impact on the quality of the monitoring operation is likely to be small.

Figure 10:
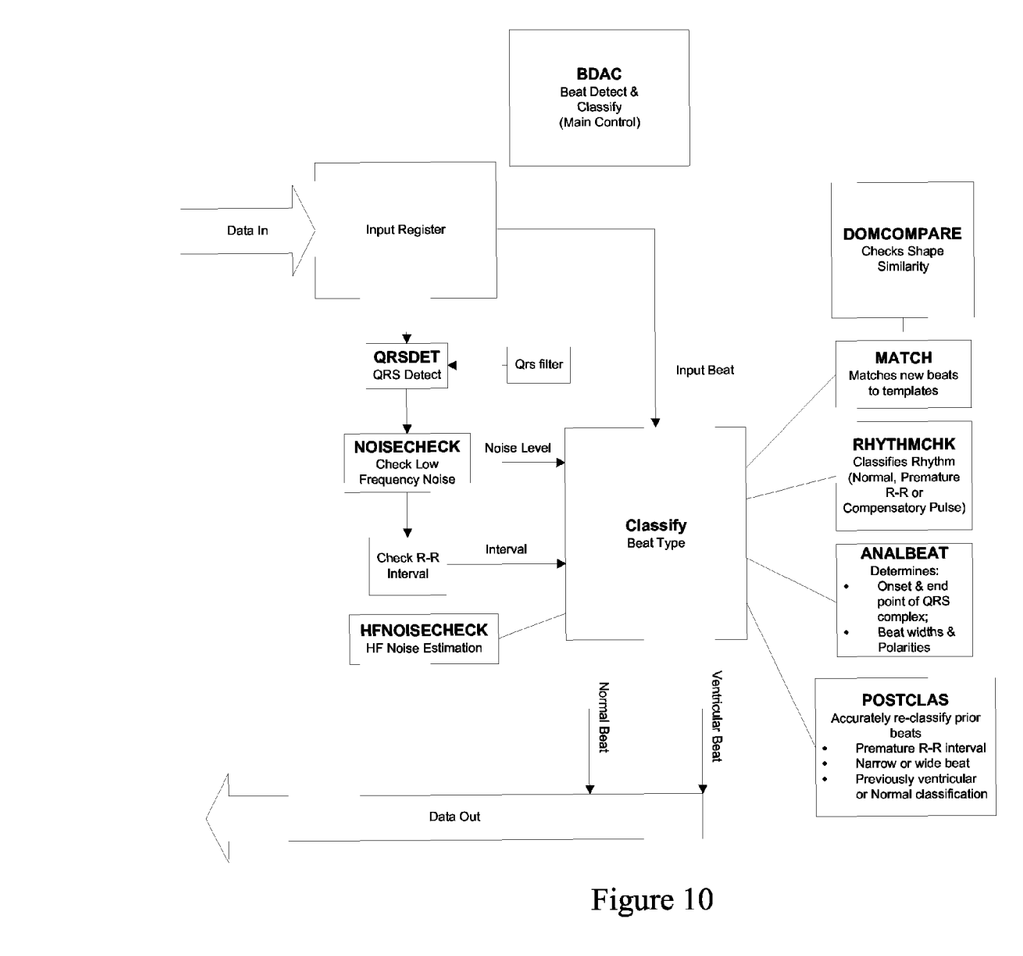
FIG. 10 illustrates the OSEA software architecture implemented at a base station of the system of FIG. 1.

With reference again to FIG. 4, the functional architecture of the base station 4 (a PDA in this example) is illustrated. The PDA will implement a method to determine the characteristics of a heartbeat. The OSEA software is one such example of this, although different vendors can implement their own analysis software to give them commercial advantage. The OSEA software flow is shown in FIG. 10. When not in analysis mode, the PDA merely datalogs the beat and template information so that should an event occur more detailed history is available for the cardiologist. When an alarm condition is received which indicates the need for an ECG analysis, the full software routine is enabled using the incoming ECG data that contains current and historical data. As well as blocks for recording a history of matched template IDs, the base station comprises blocks for analysing preconditioned ECG data received from the digital plaster. More particularly, it comprises blocks for: feature extraction, beat classification, and template generation. These implement the functionality of the OSEA model for template generation. Each time a new template is generated by the base station 4, the template is transmitted to the digital plaster over the downlink channel where it is stored in the template memory.

As described above, to compensate for the characteristics of a beat changing with time, the determined template is modified ("averaged") using a percentage of the difference between the current beat and a matching beat template. After some time, the template stored at the plaster can diverge significantly from that stored in the second part (PDA), so the template memory must be uploaded periodically to the PDA to update the PDA memory.

The required functionality for the base station may be implemented purely as a software application residing on a standard hardware platform, e.g. a smart phone or PDA. Since the computational burden of classifying new beat shapes is shifted to the base station where power and processing availability are relatively high, the processing effort required at the digital plaster is much reduced, allowing a significant reduction in power consumption to be achieved at the base station.

When a new digital plaster is activated by a user, e.g. by connecting a battery to the circuit, the plaster establishes a bidirectional communication link with the base station. At this stage, the plaster has no templates stored in its template memory, and therefore every detected beat is unmatched and is sent to the bases station over the communication link. The base station will determine from the sent data that the plaster has no stored templates. If the base station has any templates in its own memory, indicating that it has been used with previous digital plasters, it will immediately send these to the plaster on the downlink. The plaster will then continue with the template matching process for subsequent beats. If the base station has no templates stored, indicating that the new plaster is the first used plaster, the base station will begin the process of template generation using the received beats. These will be transmitted to the digital plaster immediately upon generation. It will be appreciated that as the plaster receives more and more templates, matches will become more common and the rate at which beats are sent to the base station will fall. [The base station may be provided with a reset function which, when activated, erases templates from its memory, allowing a pre-used base station to be given to a new patient.]

It will be appreciated by the person of skill in the art that various modifications may be made to the above described embodiments without departing from the scope of the present invention. For example, whilst the embodiments described above make use of the OSEA model to detect and classify beats, other models may be used.

The invention claimed is:

1. An apparatus for recording a physiological signal from a patient, the apparatus comprising:
   a first part comprising
      a first wireless transceiver,
      a memory for storing a plurality of signal segment templates, an input for receiving an electrical signal, and
      processing means for segmenting a received electrical physiological signal into signal segments, for determining, in a matching operation, whether or not each signal segment matches one of said plurality of signal segment templates that are stored, for storing data including identities and numbers of occurrences of matched templates in said memory together with any signal segments for which a matching template is not found, and for causing said first wireless transceiver to periodically transmit the stored data over a wireless link;
   a second part comprising
      a second wireless transceiver for receiving data transmitted from said first part over said wireless link,
      a memory for storing the received data or other data generated using the received data, and
      processing means for generating signal segment templates using said received data, and for causing said second wireless transceiver to transmit to the first part the generated signal segment templates.

2. The apparatus according to claim 1, wherein the processing means of the first part is arranged to analyze a signal segment for abnormalities and to cause the signal segment to be transmitted to the second part if an abnormality is detected, even if a template match has been found.

3. The apparatus according to claim 1, wherein said processing means of the first part is arranged to record in said memory of the first part a sequence of recent signal segments for use in subsequent analysis.

4. The apparatus according to claim 1, wherein said first part is arranged to detect when the first part is out of communication range or otherwise unable to communicate with said second part and in such an event to store data which would otherwise have been transmitted to the second part, and to detect when the second part is able to communicate again, and thereafter send the stored data.

5. The apparatus according to claim 1, wherein said processing means of the second part is arranged to receive signal segments transmitted from the first part, and to use these segments to generate or modify signal segment templates for transmission to the first part.

6. The apparatus according to claim 1, wherein the processing means of the second part is arranged to cause generated or modified templates to be stored in the memory of the second part and to synchronize the plurality of signal segment templates stored in the memory of the first part with those stored in the memory of the second part.

7. The apparatus according to claim 1, wherein the processing means of the first part is arranged to cause signal segment templates stored at the first part to be modified in dependence upon received signals, and to synchronize the signal segment templates stored in the memory of the first part with those stored in the memory of the second part.

8. The apparatus according to claim 1 for monitoring a mammalian ECG, wherein said signal segments contain a single heartbeat.

9. The apparatus according to claim 8, wherein said first part comprises two or more electrodes coupled to an input for providing an ECG signal.

10. The apparatus according to claim 8, wherein the processing means of the first part is arranged to determine a RR interval of an ECG signal.

11. The apparatus according to claim 10, wherein the processing means of the first part uses the RR interval to detect abnormalities in ECG segments.

12. The apparatus according to claim 8, wherein said first part is configured to be placed in contact with skin, and said second part is a body wearable part.

13. A method of monitoring a physiological condition, the method comprising:
   at a first part
      receiving a signal indicative of said physiological condition;
      segmenting the signal into successive signal segments;
      comparing each signal segment against one or more of a set of signal segment templates and identifying matching templates;
      periodically sending identities and numbers of matching templates together with any signal segments for which a matching template is not found, via a wireless communication link to a second part;
   at the second part
      storing received data or data generated from the received data;
      using said received data, to generate new signal segment templates and transmitting these via said wireless communication link to the first part,
   and at the first part
      storing received new signal segment templates for subsequent use.

14. The method according to claim 13 comprising storing data at the first part when the second part is out of range or otherwise unable to communicate with the first part, and sending the stored data to the second part when communication is resumed.

* * * * *